US006582470B1

(12) United States Patent
Lee et al.

(10) Patent No.: US 6,582,470 B1
(45) Date of Patent: Jun. 24, 2003

(54) SURFACE MODIFICATION OF MEDICAL IMPLANTS

(75) Inventors: Dosuk D. Lee, Brookline, MA (US); Atul Nagras, Somerville, MA (US)

(73) Assignee: Etex Corporation, Cambridge, MA (US)

( * ) Notice: Subject to any disclaimer, the term of this patent is extended or adjusted under 35 U.S.C. 154(b) by 0 days.

(21) Appl. No.: 08/786,869

(22) Filed: Jan. 22, 1997

Related U.S. Application Data

(63) Continuation-in-part of application No. 08/589,409, filed on Jan. 22, 1996, now Pat. No. 5,843,289.

(51) Int. Cl.⁷ .................................................. A61F 2/02
(52) U.S. Cl. ................................................. 623/23.55
(58) Field of Search ................................ 623/16, 23.58, 623/23.59, 23.6, 23.53, 23.54, 23.55; 433/201.1, 173, 175

(56) References Cited

U.S. PATENT DOCUMENTS

| | | | |
|---|---|---|---|
| 3,852,045 A | 12/1974 | Wheeler et al. | 428/566 |
| 3,905,777 A | 9/1975 | Lacroix | 428/550 |
| 3,994,793 A | 11/1976 | Harvilchuck et al. | 204/192.25 |
| 4,203,800 A | 5/1980 | Kitcher et al. | 156/643 |
| 4,542,539 A | 9/1985 | Rowe, Jr. et al. | 623/16 |
| 4,547,260 A | 10/1985 | Takada et al. | 156/643.1 |
| 4,553,272 A | 11/1985 | Mears | 623/1 |
| 4,644,942 A | 2/1987 | Sump | 623/16 |
| 4,650,543 A | 3/1987 | Kishita et al. | 156/643 |
| 4,654,314 A | 3/1987 | Takagi et al. | 501/82 |
| 4,659,331 A | 4/1987 | Matthews et al. | 623/20 |
| 4,743,256 A | 5/1988 | Brantigan | 623/17 |
| 4,790,851 A | 12/1988 | Suire et al. | 623/16 |
| 4,812,120 A * | 3/1989 | Flanagan et al. | 433/173 |
| 4,818,559 A | 4/1989 | Hama et al. | 427/2 |
| 4,865,603 A | 9/1989 | Noiles | 623/18 |
| 5,164,331 A | 11/1992 | Lin et al. | 437/192 |
| 5,176,792 A | 1/1993 | Fullowan et al. | 156/652.1 |
| 5,246,530 A | 9/1993 | Bugle et al. | 216/56 |
| 5,258,098 A | 11/1993 | Wagner et al. | 156/645 |
| 5,277,750 A | 1/1994 | Frank | 156/643 |
| 5,282,861 A | 2/1994 | Kaplan | 623/16 |
| 5,380,547 A | 1/1995 | Higgins | 427/2.26 |
| 5,456,723 A | 10/1995 | Steinemann et al. | 623/16 |
| 5,843,289 A * | 12/1998 | Lee et al. | 204/192.3 |
| 6,033,582 A * | 3/2000 | Lee et al. | 204/192.32 |

FOREIGN PATENT DOCUMENTS

| | | | |
|---|---|---|---|
| DE | 4206490 | * | 9/1993 |
| EP | 0388576 | * | 9/1990 |
| EP | 0447744 A | * | 9/1991 |
| EP | 0 606 566 A1 | | 7/1994 |
| GB | 2 257 147 A | | 1/1993 |
| WO | WO 86/06617 | * | 11/1986 |
| WO | WO 94/25637 | | 11/1994 |

* cited by examiner

Primary Examiner—David J. Isabella
(74) Attorney, Agent, or Firm—Hale and Dorr LLP

(57) ABSTRACT

A method of obtaining a porous titanium surface suitable for medical implants is provided. The titanium surface is exposed to a plasma comprising a reactive plasma gas, the reactive plasma gas comprising an active etching species and a sputtering gas. The plasma conditions are effective to modify the titanium surface and provide surface porosity. The plasma conditions are effective to non-uniformly etch and sputter the titanium surface.

25 Claims, 9 Drawing Sheets flat Ti plate flat Ti plate at tail – threaded implant unthreaded implant – tail section screw (head)

head section at head between thread masked / substrate interface - flat Ti plate head of implant screw (tail)

tail – unthreaded implant unthreaded implant - midsection on thread at tail

SURFACE MODIFICATION OF MEDICAL IMPLANTS

This application is a continuation-in-part application of U.S. Ser. No. 08/589,409 filed on Jan. 22, 1996, now U.S. Pat. No. 5,843,289 and similarly entitled "Surface Modification of Medical Implants".

FIELD OF THE INVENTION

This invention relates to a method for modifying surfaces of metallic articles, such as medical devices. This invention further relates to treatment of implant surfaces to achieve desirable rough and microporous surface features which enhances bone ingrowth and thus establishes a strong mechanical bond with the implant.

BACKGROUND OF THE INVENTION

Titanium, either pure or as an alloy with a few percent aluminum and vanadium, is used as the metal for bone implantation in knee and hip joints. Titanium is commonly used because of its mechanical properties and also its bio-compatibility. However, titanium does not form a direct chemical bond with bone, which can sometimes cause loosening and failure of the implant. Rough and porous implant surfaces permit bone and bone cement to penetrate the surface pores and ideally provide a strong mechanical bond with the implant.

Irregular and rough implant surfaces with certain characteristic features can effectively promote bone ingrowth and directly bond with bone, thus enhancing long term implant stability. European Patent No. 038 8576 reports that it is desirable to have a surface macro-roughness with pore sizes of about 10–20 $\mu$m with a micro roughness superimposed thereon with a pore size of less than 2 $\mu$m. Thus, an implant surface with macro-roughness and micro-porosity is highly desirable and can effectively promote bone ingrowth and fixation. This dual feature surface can also be useful when bone cement material is used to adhere implants to bone (i.e., polymethyl(methacrylate)).

Achieving the desired balance of macro- and micro-porosity has not been easy. Presently, modification of implant surfaces can be classified into two distinct groups: (a) surface modification by application of a coating of rough and/or porous material; and (b) surface modification by bulk implant surface treatment.

Porous coatings disclosed in the prior art include diffusion bonded metal fiber coatings produced from titanium wire in the form of random, rough metal fibers. Pressure sintering of spherical titanium metal powders or beads on implant surfaces also has been used to produce macro-porosity (U.S. Pat. No. 4,644,942). Thermal plasma spray processes have also been used to deposit porous coatings (U.S. Pat. No. 4,542,539). Commercially pure titanium or titanium alloy powders are partially melted in the plasma flame and the molten particles impact the implant surface at high speeds. These powders rapidly quench on the surface and adhere to the implant metal thus yielding a rough surface. Another porous coating reported in the prior art is a perforated metal foil applied to a solid metal core (U.S. Pat. No. 3,905,777).

In all of the above prior art devices, an interface between the metallic core and the porous surface results. In order to be used as a implant device, the interface between the coating and the implant substrate must be strong and stable. Interfacial failure during implant insertion or after prolonged use of the implant can result in loose metal particles which can become a source of contamination in the adjacent tissue and may also cause the failure of the implant.

Yet another method of imparting surface roughness to a metallic implant device is to treat directly the surface of the solid metallic core. U.S. Pat. No. 4,865,603 discloses a method of surface treatment in which the outer surface is subjected to serial machining processes which results in a complex surface topology. A laser beam of selected power and pulse duration has been used to drill cavities on an implant surface. (U.S. Pat. No. 5,246,530). Precise positioning equipment is necessary to process the implant in both of these methods. An additional major disadvantage of the laser process is that it only provides macro cavities for bony ingrowth. Finally, EP 388 576 discloses a method of aqueous acid treatment, which has been used to achieve a rough and porous surface on implants for bone ingrowth. However, titanium hydride and other undesirable surface artifacts are formed as a result of the acid-metal reaction.

Thus, there remains a need to provide effective surface modification techniques which provide a surface suitable for bone ingrowth, which possesses strength and structural integrity and is free of surface contamination.

Plasma treatment of titanium-containing surfaces is known and used in the semiconductor industry, primarily for the etch removal of titanium-tungsten layers in semiconducting devices. See, U.S. Pat. Nos. 5,164,331 to Lin et al. and 4,203,800 to Kitcher et al. The references are directed to removal of TiW alloy to expose the underlying layers in a semiconductor device. The material is desirably removed at a constant, even rate across the entire exposed surface. Further, the resultant surface is desirably smooth and even. These and other similar prior art methods do not contemplate a process for surface treating a bulk titanium work piece so as merely to alter the surface characteristics or in particular to provide a rough, porous surface.

SUMMARY OF THE INVENTION

It is an object of the present invention to provide an article and method of manufacture of an article having a porous surface suitable for use as an implant device.

It is an object of the present invention to provide a porous surface on an implant device with high structural integrity.

It is a further object of the present invention to provide a porous surface on an implant device with high surface purity and without the formation of surface contaminants.

It is yet a further object of the present invention to provide an article and method of manufacturing an article which has a porous surface exhibiting macro- and micro-roughness.

The present invention uses a process for modifying the implant surface to form a porous surface with characteristic macroroughness and microporosity, which is close to naturally the surface structure of occurring bone tissue. The method of the invention includes exposing a titanium surface to a plasma comprising a reactive plasma gas including an active etching species and a sputtering ion. Predetermined plasma conditions are used to modify the titanium surface and provide surface porosity.

The present invention also includes exposing a titanium surface to a plasma comprising a reactive plasma gas including an active etching species and a sputtering gas. Predetermined plasma conditions are used to effect non-uniform etching and non-uniform sputtering of the titanium surface. The titanium may be commercially pure titanium or a titanium alloy.

By "non-uniform etch rate" and "non-uniform sputter rate", as those terms are used herein, it is meant that the etch and/or sputter rate are not constant or even within a given cross-sectional area of the work piece surface (geographic non-uniformity). It may additionally include rates which are variable over time (temporal non-uniformity).

By "reactive plasma gas", as that term is used herein, it is meant to include both a gas mixture which is introduced into the plasma chamber and the plasma gases which result therefrom. Thus, the reactive plasma gas includes an active etching species and the halide gases from which it is formed; the reactive plasma gas likewise refers to a sputtering gas introduced into the plasma and the bombarding ions generated therefrom in the plasma.

In a preferred embodiment, plasma conditions are effective to redeposit sputtered species onto the titanium surface. In another preferred embodiment, plasma conditions are effective to sputter off oxygen adsorbed on the titanium surface during exposure of the surface to the plasma. In yet another preferred embodiment, a sputtering target is introduced into the plasma, said sputtering target comprising a masking element, such that the masking element is deposited onto the titanium surface during exposure of the surface to the reactive plasma gas. The plasma may be effective to take advantage of masking properties of alloyed elements in the work piece or of variable etch rates among surface deposited species on the work piece.

The present invention provides a rough and/or microporous implant surface without any contamination or deleterious effect on the bulk properties of the implant. An advantage of this invention is that the rough and porous surface is integral to the implant metal and no chemical byproducts or artifacts are formed by this method. The article comprises a metallic substrate; and a surface comprising metallic filamentous elements having a length of about one to fifteen micrometers, the filamentous elements integral with the substrate at a first end and extending in a substantially outward direction from the substrate. The article may be characterized by the filamentous elements characterized by a fused appearance or by filamentous elements characterized by an arched configuration in which the filamentous elements appear fused at a point distal from the substrate.

In one embodiment of the invention, filamentous elements are located at the substrate with a density of about 1–40 filamentous elements/$\mu m^2$. In another embodiment of the invention, the arched filamentous elements are located at the substrate with an arch density of about 0.01–10 arches/$\mu m^2$. In yet another embodiment of the invention, filamentous elements are located and arranged at the substrate so as to have the appearance of a ridge or wall. The ridge or wall may be separated from an adjacent ridge or wall by a distance of about 0.5 $\mu$m to about 2 $\mu$m.

By a "porous" as that term is used herein, it is meant a surface which is not a flat or dense surface and which exhibits a complex surface morphology. It does not require the presence of actual "pores" in the conventional sense.

By "filamentous" as that term is used herein it is meant an elongated feature extending in a substantially outward direction from the substrate surface, having a round, flattened or tape-like appearance. The individual filamentous features may be free standing or they may be fused or otherwise agglomerated in the final surface structure. Fused or agglomerated filamentous substructures provide the surface morphology of the surface of the inventive devices.

The roughened surface and microporosity on the surface yield an increase in the surface area. Such an increased surface area may also provide an ideal substrate for chemically bioactive coatings (for example, hydroxyapatite), thereby improving adhesion of the coating to the implant surface. Further, the uneven surface morphology, with its undercuts and deeply etched gaps, are a source of physical interaction with host site to secure a medical implant and promote osseous ingrowth.

The method of the invention may be readily adapted to non-titanium surfaces, by control of the processing variables identified in the present invention.

BRIEF DESCRIPTION OF THE DRAWING

For a fuller understanding of the invention, reference is made to the following description taken in conjunction with the accompanying drawings, in which.

DETAILED DESCRIPTION OF THE INVENTION

Figure 1:
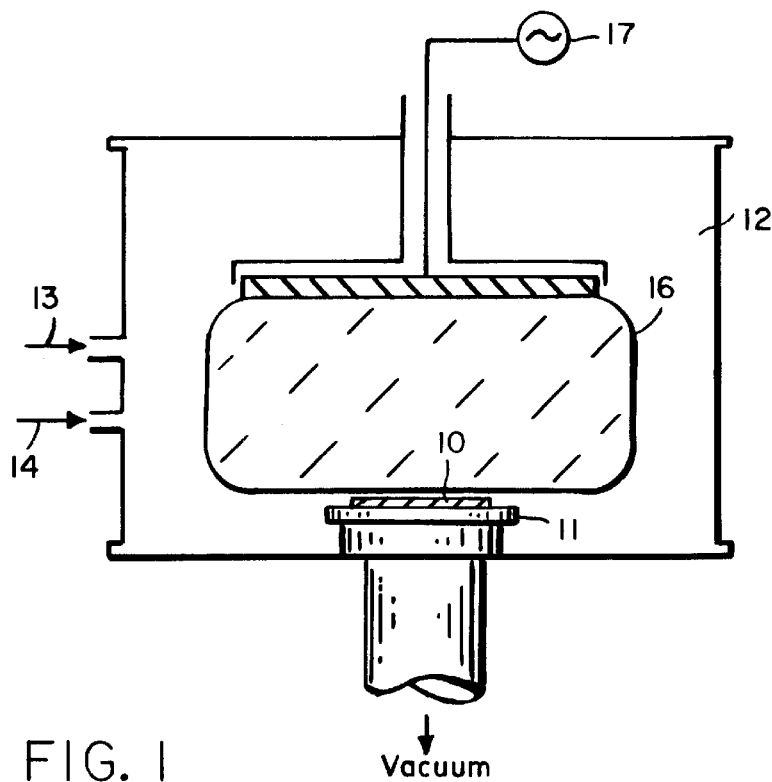
FIG. 1 is a schematic cross-sectional view of the plasma apparatus used in practice of the invention.

The present invention uses a reactive plasma etching process to provide an article having a roughened, filamentous or porous surface which is particularly well-suited for bone ingrowth. The implant device is preferably made of titanium or a titanium alloy, such as alloys with vanadium and/or aluminum; however, as is seen herein below, the process may be readily adapted to surface treatment of other metal by appropriate selection of reactive plasma species and plasma conditions.

A plasma is a gas (or cloud) of charged and neutral particles exhibiting collective behavior which is formed by excitation of a source gas or vapor. A reactive plasma generates many chemically active charged (ionic) and neutral (radical) species. These charged and neutral species are more active etchants than the original source gas. The reaction of the active neutral and ionic species on the surface of a work piece etches, or removes, portions of the surface. The physical striking of ions on the surface of the implant work piece (i.e., sputtering) further enhances the etch rate. Thus in a "reactive plasma" process, both physical sputtering of ions and dry chemical etching by the active neutral and ionic species occurs. Not all of the surface atoms liberated by sputtering or reactive etch are immediately removed from the system and, if conditions are favorable, considerable redeposition of the atoms of the titanium surface may occur. Further, the different atoms present on the exposed surface will undergo reactive chemical etching and physical sputtering at different rates. Thus, the etch rate and redeposition rate may be controlled by controlling the reactive plasma feed composition, work piece composition, gas pressure, plasma power, voltage bias across the sheath, reactor geometry, workpiece dimension and process time.

For application to medical implant devices, it is desirable that the mode of etching does not introduce further contaminants onto the surface of the work piece. Thus, according to the invention, a fluorine- or chlorine-containing source gas may be used to generate an active etching chlorine or fluorine species. The active species may be a radical or charged species. Although iodine-containing gases have not been used to etch titanium, they may be useful to treat other metal surfaces. Titanium reacts with the active etchant species of Cl and F radicals to form a volatile titanium halide which is pumped away by the system. For example, $TiCl_4$ has an evaporation temperature of 135° C.; and $TiF_4$ has a sublimation temperature of 285° C. at atmospheric pressure. Under low pressure operating conditions, these volatile halides may evaporate at ambient temperatures. Thus, no impurities are introduced into the work piece by the etching process, as all by-products are rapidly removed from the work piece surface.

A wide range of fluoro- and chloro-containing compounds may be used to generate the active chlorine or fluorine species. Suitable compounds include, by way of example only, $CF_4$, $Cl_2$, $BCl_3$, $SF_6$, $CHF_3$, $CHCl_3$, $XeF_2$, $CCl_4$, and fluorocarbons commercially available as Freon 11, Freon 12, Freon 13 and Freon 115. Two or more compounds may be used to generate a mixture of reactive radicals or to vary the concentration of a particular reactive radical with changing plasma conditions.

The active etching species is used in combination with a heavier bombarding or sputtering ion and, optionally, lighter species such as oxygen, helium and nitrogen. Bombarding ions of a noble gas and/or also some complex reactive ions further enhance the process of the formation and sublimation of the titanium halide at lower temperatures. The ion bombardment assists desorption of metal-halides formed on the surface as they are knocked off or imparted with enough energy to leave the surface. This may be contrasted to a wet chemical etching process (e.g. mineral acid bath) in which chemical by-products of the etch remain on and contaminate the work piece surface.

A sputtering gas which can generate heavy bombarding ions is included in the reactive plasma gases to enhance the reactive etch by physical sputtering of the work piece surface. Suitable bombarding ions may be generated from the heavier noble gases, such as Xe, Kr and Ar, or heavier reactive halogen compounds, such as by way of example only, $BCl_3$, $XeF_2$, $SF_6$, etc. The reactive halogen compounds may of course also be the source of the reactive chlorine or fluorine species.

Additional lighter gases may be included in the reactive plasma gas, such as helium or nitrogen. These ions affect the ion recombination rate of reactive etching gas. Oxygen may be added to the reactive plasma gases to modify the etch rate of the plasma gas. Oxygen will not effect the etch rate of fluorine-based plasmas; however, it retards the etch rate of chlorine-based plasmas. Thus, where oxide is formed on the surface of the work piece surface, etching is hindered.

The reactive plasma gas described above may be used in accordance with the method of the invention to treat the surface of a work piece and thereby obtain a rough surface having a filamentous substructure. As illustrated schematically in FIG. 1, a work piece 10 is initially ultrasonically cleaned with an appropriate solvent (eg., acetone, alcohol) to remove any loose particles from the surface and thoroughly dried. The work piece is then held in a suitable holder 11 and placed in a vacuum chamber 12. The holder 11 and work piece 10 may rest on a base of the reaction chamber in electrical connection with the non-power electrode; or they may positioned in towards the center of the plasma cloud, e.g., suspended by a wire, preferably maintaining electrical connection with the non-power electrode. It is contemplated that the workpiece may be rotated or otherwise moved during the etching process. The chamber is evacuated by vacuum pumps (not shown) to about $5 \times 10^{-5}$ torr or lower. A chloro- or fluoro-containing gas and a sputtering gas (and other optional gases) are introduced into the chamber by respective inlets 13 and 14. The pressure inside the chamber is maintained between about 5 and about $100 \times 10^{-3}$ torr. A plasma 16 is ignited and created inside the chamber by a plasma power source 17. The plasma contains high speed ions and neutral species. These ions bombard the surface of the work piece and cause physical sputtering (removal of atoms from surface). Reactive ions and neutral species chemically etch the surface.

Figure 2:
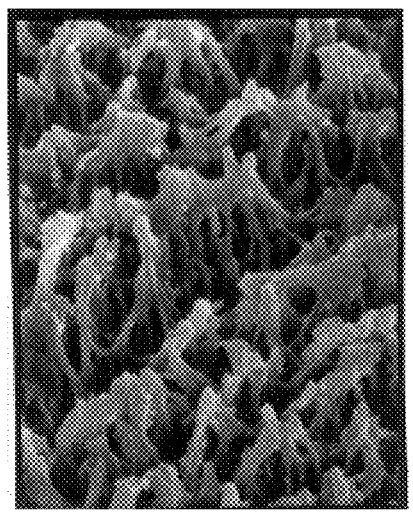
FIG. 2 is a photomicrograph of a titanium surface after treatment according to the invention at 10,000× magnification.
Figure 3:
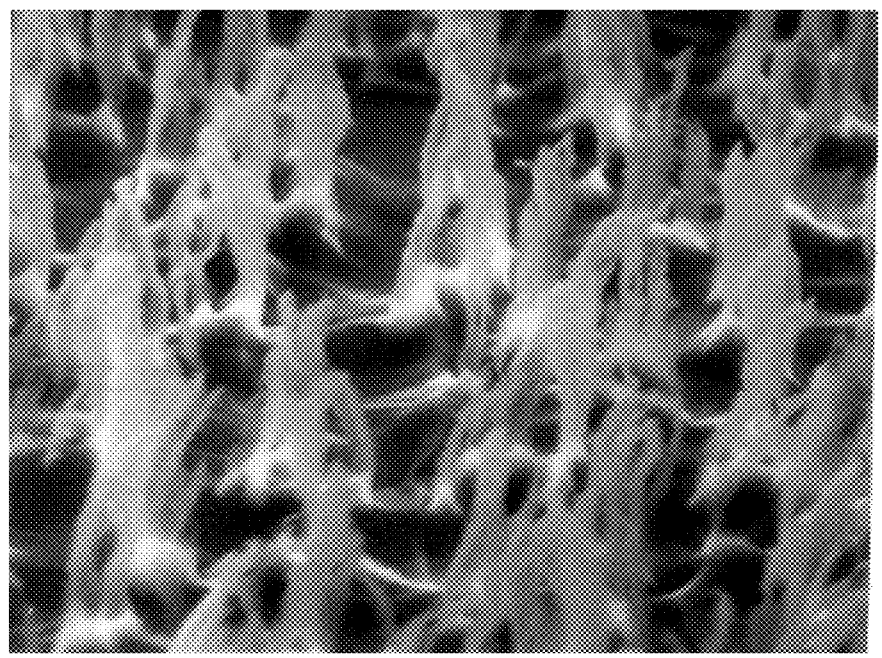
FIG. 3 is a scanning electron photomicrograph (SEM) of a titanium surface after treatment according to the invention at 12,000× magnification.

The reactive gases are stopped and the chamber is then cleaned with a $O_2$ plasma. The work piece is then removed from the chamber and is cleaned in an ultrasonic bath to remove any surface residue or contamination. A surface having the morphology such as shown in the photomicrograph (10,000× magnification) in FIG. 2 is obtained. The surface may also be described as having the appearance of coral or cancellous bone, which is recognized as having desirable properties as a bone substitute material. The surface is characterized by a large surface area to mass ratio, because of the extended open network on the surface. The work piece is preferably a medical implant device.

A variety of surface morphologies can be produced by the inventive method. The array of surface morphologies attainable is best described as being derived from a filamentous unit substructure. For a given set of etching parameters, a morphology comprising a characteristic pattern of filamentous elements or substructures is observed. The filamentous elements or substructures are grouped on the substrate surface in unique and characteristic fashions to form "assemblies" which may be lamellar, e.g., corrugated fence- or ridge-like, or which may be tufted, e.g., coral- or sponge-like.

Filamentous substructures appear clustered and fused with one another into semi-regular morphological assemblies which may be interspersed between deeply etched regions or gaps on the article surface. A given surface morphology may be described in terms of the dimensions of the filamentous substructure, the degree and nature of filamentous fusion and clustering within the morphological assemblies and the size and spacing of deeply etched gaps. A variety of typical surface morphologies which can be produced by the current invention are described below in these terms and shown in FIGS. 2–16. These morphological descriptions are descriptive only and in no way are meant to imply how the structures are actually formed. Specifically, the terms "fused" or "fusion" does not imply that initial subunit filaments are formed individually and then subsequently fused.

Filamentous structure. The filamentous substructure is exemplified in FIG. 3, which is a scanning electron micrograph (SEM) of the surface of a flat titanium plate prepared by the plasma etching methods of the instant invention. In this figure, distinct filament-like structures 50 are observed approximately 1–3 $\mu$m long with a diameter on the order of 0.05–0.5 $\mu$m. The filaments are present at a density of about 1–4/$\mu$m$^2$ on the article surface. Many of the filamentous structures in the micrograph have an appearance of being composed of the fusion of smaller filamentous subunits (although there is no representation that this is how they actually are made), and some are ribbon-like in shape, e.g., see FIG. 14. The degree of fusion may be to the extent that the surface appears as a series of ridges with are rather dense, but which retain a filamentous appearance on the ridge walls, see, FIG. 12. The filamentous elements emerge from low ridges 52 (0.1–0.9 $\mu$m) on the implant surface. The combination of filamentous substructures on a ridged substrate surface may provide a combination of macro- and micro-surface roughness which has been demonstrated to be desirable for osseointegration of medical implants.

Figure 4:
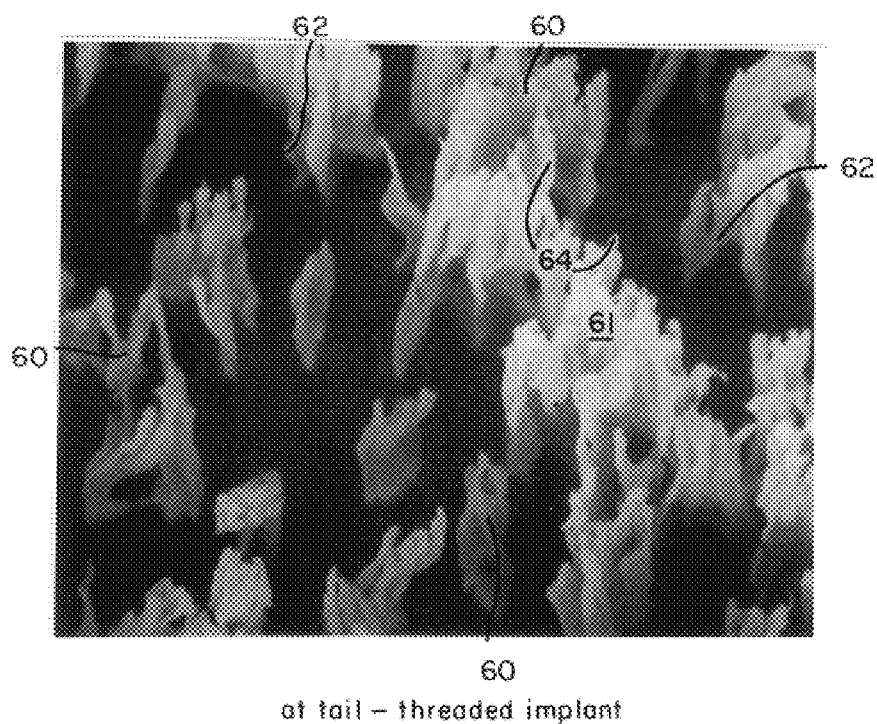
FIG. 4 is a scanning electron photomicrograph (SEM) of a titanium surface after treatment according to the invention at 10,000× magnification.
Figure 5:
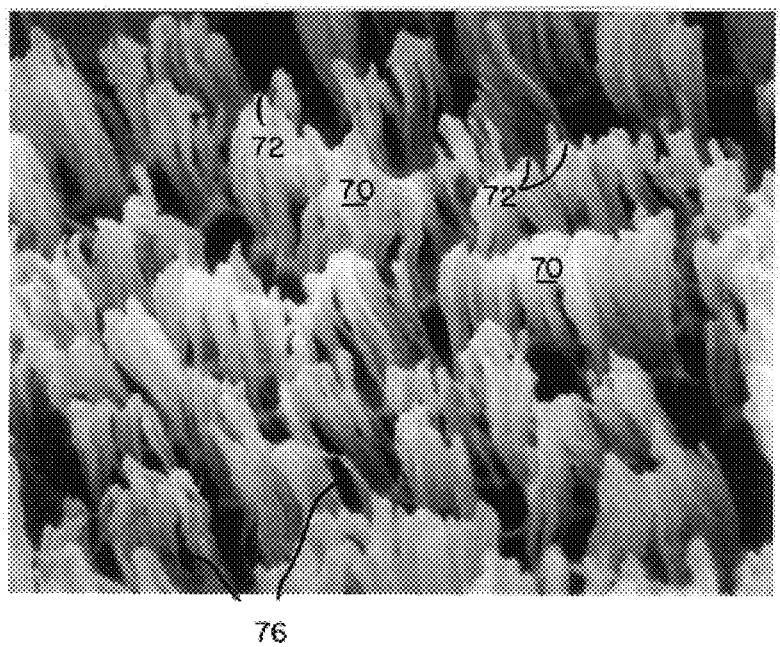
FIG. 5 is a scanning electron photomicrograph (SEM) of a titanium surface after treatment according to the invention at 10,000× magnification.

Fused appearance. Many of the surface features observed following etching according to the invention appear as clusters of extensively fused filaments. FIG. 4 was taken from the tail of an etched threaded implant, i.e., a screw. Etching was performed as described in Examples 1 and 2 with the sample balanced on its head resting on the non-power electrode. The filamentous substructure is clearly visible. In this sample the filaments 60 are at a density of about 2–5/$\mu$m$^2$ and tend to be more ribbon-like in appearance. The larger structures 61 appear as ribbon-like filaments 60 fused at the base 62 with free ends 64 of about ~1 $\mu$m in length projecting from the top. FIG. 5 demonstrates this feature where the clustered filaments 70 (2–4 $\mu$m in length, 4–10/$\mu$m$^2$) are fused throughout their length with only short tips or bumps 72 protruding distally from the substrate surface. In FIG. 5 the filamentous substructures occasionally appear unfused in regions proximal to the substrate surface near the base but are fused in the distal regions or at the tips forming holes or arch like structures 76.

Figure 6:
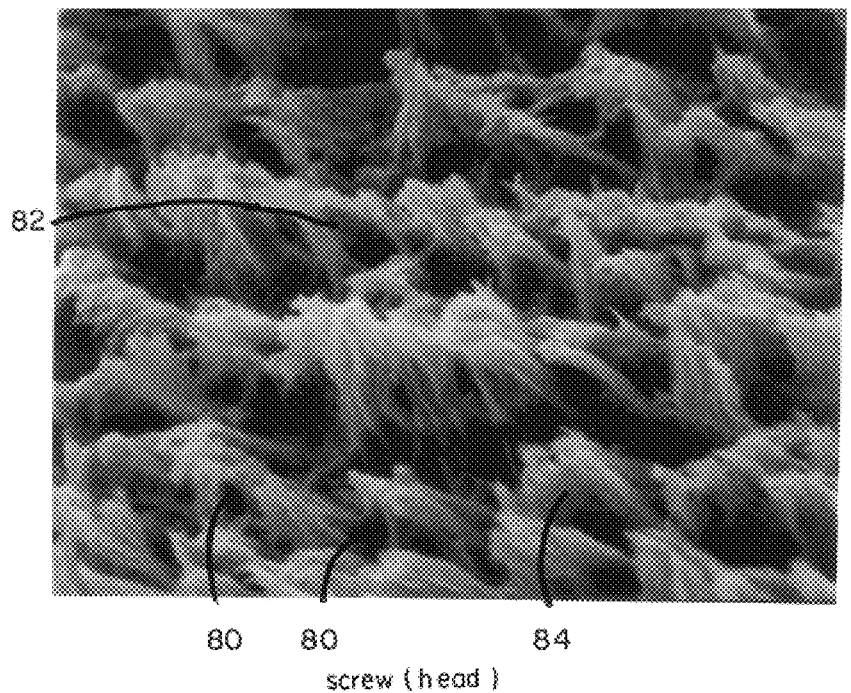
FIG. 6 is a scanning electron photomicrograph (SEM) of a titanium surface after treatment according to the invention at 10,000× magnification.

Arching. With reference to FIG. 8, the arching morphology is defined as a hole or pore 80 which occurs in a surface assembly which is most often characterized by distally fused filamentous substructures with at least a portion of the more proximal aspect of the filamentous substructures being distinct or unfused resulting in a hole or pore. Pores may range up to 1 $\mu$m preferably up to 0.5 $\mu$m and most preferably from 0.05 to 0.5 $\mu$m. Arching may be a predominant morphological feature or it may occur infrequently. Arches may be open on both sides eg, 82 or closed on one side to form an alcove-like surface feature, e.g., 84. Arches are believed to be an optimal structure for promoting the interaction of the treated article with living tissue and thus are a preferred surface feature on the articles of the invention. FIG. 6 represents a sparsely arched morphology (arch density= 0.005–0.06 arches/$\mu$m$^2$), whereas FIG. 2 is a micrograph of a densely arched, preferred embodiment (arch density= 0.01–10 arches/$\mu$m$^2$), Clustering. The surface features of the article may be further described as a function of the "clustering patterns" of the fused filamentous elements. Specifically filamentous elements may cluster or be arranged linearly to produced a lamellar-like surface morphology 90 such as in FIG. 7. The surface in this figure is characterized by rows 92 of fused filaments 94 with interposed deeply etched gaps 96 (0.25–2.0 $\mu$m deep). In other cases the clustered filaments 100 may appear leafy and irregular separated by fairly wide (1–4 $\mu$m) deeply etched gaps 102 (See FIG. 8).

Deeply etched gaps. In some morphologies deeply etched gaps are interposed between ridges or rows having a clustered filamentous morphology. Generally these gaps extend down to the base of the filamentous ridges and represent the full extent of the depth of the etching process. Parameters which favor the production of deep edged gaps are: long etching time, high RF power, and surface geometry.

Depth. The filamentous surface morphology can be prepared with depths (as measured from an outer edge to-the unetched solid titanium base) from 1 to 15 $\mu$m. The various morphological features described above will be present at various densities depending upon the specific etching parameters employed.

For the anchoring of biological devices meant to osteointegrate with adjacent bone in the host, the following surface parameters have been found to be particularly useful.

| Filamentous substructure: | |
| --- | --- |
| filament length: | 2–3 $\mu$m |
| filament diameter: | 0.1–0.5 $\mu$m |
| filament density: | 1–40 $\mu$m$^2$ |
| filament arch density: | .01–10 arches/$\mu$m$^2$ |
| filament clustering: | homogenous without dramatic clustering patters |
| deeply etched gaps: | 1–2 $\mu$m without any prominent pattern. |

Following etching, the surface may be post processed to further alter surface morphology. Post etching processing treatments include but are not limited to treatment with acid, heat, abrasion, secondary plasma etches or coating with particulate, liquids, solids or gels. A particularly useful post-etch processing is the coating of the etched work piece with a calcium phosphate surface. The calcium phosphate may be applied in either an amorphous or crystalline structure with one or more calcium phosphate phases present.

The article of the invention is preferably a medical implant. Medical device implant components which contact bone and for which improved osseointegration afforded by instant invention may prove advantageous include joint replacement components such as knee-tibial, hip-femoral, knee-femoral, hip acetabular, and knee-patellar components. Dental and orthopedic screws such as screws for fixation of trauma devices, screws for fixation of orthopedic implants, and pedicle screws may all be advantageously treated by the current invention. Other orthopedic fixtures include cages for spinal interbody fusions and Kirschner wires.

Medical implant devices with a roughened surface of the invention may be secured at the implant location through the use of orthopedic cements such as PMMA or hydroxyapatite bone cements. In a preferred embodiment the cement is fully resorbable and replaced by the patients own bone. Suitable such cements are described in published PCT application PCT/US96/07273 by Lee et al.

A selective combination of the physical and chemical etching processes creates the microporosity. By proper control over the ratio of gas mixtures, gas pressure, plasma power and process time, a surface with interconnected porosity can be produced. These and other processing parameters are adjusted to predetermined values so as to achieve non-uniform sputtering and non-uniform etch rates of the surface. Etch and sputtering rates are a function of a plurality of parameters, such as, but not limited to, grains boundaries, impurities, incident ion energies, neutral species density, and gas pressure. The present invention has recognized that it is possible to adjust the etch rate (by varying incident ion energy, gas pressure, power input, etc) so as to obtain an optimal etch rate for forming porous surfaces. Where etch rates are too high or too low, a porous surface is not formed. For example, at low gas pressures, ion energies are high, collisions of sputtered atoms with neutral species are less frequent. This leads to higher etch rates (and low redeposition rates). Conversely, at high gas pressures, collisions are more frequent, leading to significant redeposition of the sputtered atoms. Thus the etch rates are slow and the surfaces are smooth. The optimal etch rate is between these two extremes.

The etch rate and the surface etch profile rate also are functions of the concentration of the active species, i.e., Cl or F, in the plasma. The plasma gas composition, and in particular,. the reactive gas to sputtering gas ratio, and plasma power determine the concentration of these active species. The normal operating frequency for reactive ion etch plasma power source is RF power at about 13.56 MHz (a frequency assigned for industrial use). However lower (100–300 KHz) and higher (microwave –2.45 GHz) frequencies can also be used as plasma power sources. RF plasmas are more efficient at generating plasma at low gas pressures, which give higher sheath voltages and therefore, higher on bombardment energies. High energy bombardment is particularly useful for insulating surfaces such as metal oxides.

Without being limited to the processes described hereinbelow, the novel spongelike, porous surface structure of the invention (as illustrated in FIG. 2) is believed to result from non-uniform sputtering and etch rates of the work piece surface. This may be achieved by one or more of the following processes occurring during reactive plasma etching.

(a) Redeposition of sputtered or etched material onto the work piece surface;

(b) Differing etch rates of titanium and alloyed elements such as Al and V in the work piece resulting in a non-uniform etch rate;

(c) Backsputtering of backing plate atoms (typically Al) causing a masking effect on the work piece surface; and (d) Selective oxide formation on the surface of the work piece resulting in a masking effect.

By masking, it is meant that the surface of the work piece is covered or masked and thus is not exposed to the plasma gas. A mask is used in the semiconductor industry in the formation of gates and other circuit features. The mask is typically a layer deposited on the surface which is not affected by the surface removal process and thereby protects the underlying surface. In the present invention, the masking effect is obtained, not by a deliberate deposition of a protective masking layer, but by features of the plasma process. These processing features may be set at predetermined values for the reactive plasma etch in order to obtain the microporosity of the invention.

The present invention identifies the factors which may be controlled during surface treatment of the titanium work piece. Microporosity is obtained by selective control over composition and gas ratio of the reactive plasma gas, the plasma gas pressure, the plasma power, the composition of the work piece and holder. One or more, but not necessarily all, of the variables may be present and set at predetermined values in any particular system.

The rate of redeposition is influenced by reactive plasma gas pressure. As the pressure of the system is increased, the density of the various species present increases as well. Species that are ionized and present in the plasma are more likely to collide with other constituent particles in the plasma, lose energy and drop back to the surface. Gases, such as helium and nitrogen, may be added to the reactive plasma gas (this is reflected in the total pressure of they system) to increase collisions and enhance the redeposition rate of the sputtered species. The sheath voltage may also affect the rate of redeposition. High sheath voltage would increase the rate of removal of Ti from the work piece surface, by increasing the energy of the bombarding species and the propensity of the active species (Cl or F) to move to the work piece surface.

The presence of oxygen on the work piece surface will also contribute to non-uniform surface modification. In addition, residual oxygen and water vapor in vacuum chamber provides oxygen. Oxygen on the surface typically is present in the form of a passivating $TiO_2$ layer which is not reactively etched by chlorine active species. The passivating layer acts as a mask to prevent reactive chemical etch of the underlying titanium surface. Thus, a reactive plasma gas having a chlorine active species and a sputtering gas will promote non-uniform surface etching. Sites on the work piece surface which contain the oxide are not etched by the chlorine active species, while surface sites where oxygen had been removed by heavy sputtering gases (and the underlying Ti layer has been exposed) would react to form titanium halide. Because the sputtering away of the surface oxygen occurs a little at a time, the underlying surface is etched at differing rates.

The use of titanium alloy for the work piece promotes a microporous microstructure as well. The non-uniform etch rate is achieved due to the uneven etch rate of the alloyed metals compared to titanium. For example, an alloy of Ti, Al and V would have the Al and V etching away faster than the Ti, resulting in an uneven, porous structure.

Backsputtering from the work piece holder may also contribute to the formation of the uneven, porous surface. While the incident ions are bombarding the work piece surface, the holder is also being bombarded by these ions. This causes atoms from the holder to be sputtered (backsputtering). These backsputtered atoms collide with gas species and may be deposited onto the work piece. If these atoms are not etched readily by the active species, they act as a mask while the work piece surface is etched away around them. Eventually, these masking atoms are sputtered away by the bombarding ions and the surface underneath is exposed to reactive etching. This masking effect at a microlevel results in a non-uniform etching rate, promoting the microporosity of the invention. It is also within the scope of the invention to intentionally introduce a masking element from sources other than the holder during the plasma etching process. For example, a second target may be positioned within the chamber for such purposes.

The present invention is thus a non-uniform dry chemical etch and redeposition process without any contamination or effect on the bulk properties of the implant. The primary advantage of this invention is that the rough, microporous surface is integral to the implant metal and that no chemical byproducts or artifacts are formed by this method.

In preferred embodiments, the surface is cleaned before plasma etching to remove all surface impurities. Conventional cleaning techniques may be used, such as ultrasonic cleaning and ultra high vacuum-compatible cleaning methods.

Titanium forms a very thin layer of native oxide ($TiO_2$) on its surface when exposed to the ambient. Chlorine gas ($Cl_2$) or the radical species Cl does not etch this native oxide. Without the removal of this native oxide the titanium underneath cannot be etched to create the desired porous surface. Thus, in embodiments which use an active chlorine plasma species, the process desirably includes a preliminary sputtering step in which the passivating $TiO_2$ layer is removed. In this process, an initial sputtering process is used to remove this extremely thin oxide layer. The sputtering step may be carried out using heavier ions, such as by way of example only, $BCl_3$, Ar and $XeF_2$. Plasma etch of titanium oxides with fluorine will remove the titanium oxide layer and therefore does not require the initial oxide "breakthrough" step.

In some embodiments, a macro surface roughness or "macroporosity" may be formed on the work piece surface before the plasma etch surface treatment of the invention. Grit or sand blasting of the surface may be used to induce macroporosity. Grit blasting and sand blasting are commonly used methods for creating a visibly rough surface. The smooth surface may be exposed to a high velocity stream of sand or grit that physically gouges away parts of the surface. This only can produce macroporosity, as the effect is limited by the particle size of the impacting sand or grit. Macroporosity is typically defined as surface features on the order of 10 or 20 microns and greater. It may provide a suitable surface, however, on which to perform the microporosity inducing surface treatment of the invention.

In another preferred embodiment, post-etching processes may be performed which improve the biocompatibility of a medical implant device. For example, the porous surface of the treated titanium work piece may be coated with a hydroxyapatite coating to enhance bioactivity at the surface. The hydroxyapatite coating may be in the range of about 100 Angstroms to about 1 $\mu$m in thickness. The thickness is chosen to maintain the microporosity. A suitable method of coating may be RF sputtering or ion beam sputtering of hydroxyapatite onto the surface. The interested reader is directed to U.S. Pat. No. 5,543,019 to Lee et al. for further details, which is herein incorporated by reference.

A medical implant having the surface described herein is ideally suited for in-growth of natural bone. Superior osseal in-growth into bone implants has been established in dogs. Titanium screws treated according to the invention were implanted in a jaw tooth socket and the bone in-growth was monitored over time by determining the % surface area contact of the screw with ingrown bone. FIG. 4 is a bar graph illustrating the percent bone contact of surface treated implants after six months in vivo. A comparison implant having a surface roughness characterized by spikes demonstrated only 38% bone contact, while the implant having the interconnecting porous surface of the invention demonstrated 55% bone contact and 54% bone contact, with and without an HA coating, respectively. See, Example 4 for details.

It will be readily apparent that the present invention may be extended to articles which are comprised of metals other than titanium. In order to obtain a porous surface for non-titanium articles, an active species which is capable of reactive etching that metal is selected and used in combination with a sputtering gas. Plasma conditions are selected to obtain an etch rate which is optimal for forming a porous surface.

It is contemplated that the surface of the present invention may find uses in areas other than the bone implant field. For example, the high surface area/low mass ratio which is possible for such as surface may be useful for applications requiring surface/incident radiation interaction, such as thermal and electron radiation. They may be particularly useful as transducers.

The invention may be understood with reference to the following examples which are presented for the purpose of illustration only and which are not intended to be limiting of the invention, the true nature and scope of which are set forth in the claims hereinbelow.

Example 1. This is an example to demonstrate modifying a planar commercially pure (CP) Ti surface.

Figure 17:
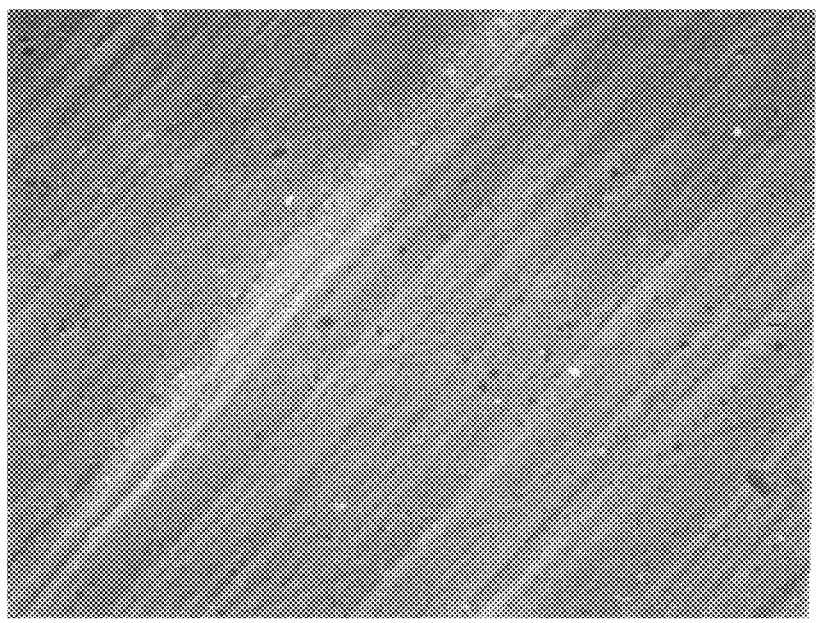
FIG. 17 is a photomicrograph of a titanium surface before treatment at a 5000× magnification.

FIG. 17 is a photomicrograph of the CP titanium surface before treatment, showing the smooth features of the work piece. Some machining marks are evident on the surface, but it is otherwise smooth and nonporous. The implant was thoroughly cleaned before it is loaded in the vacuum chamber. The implant was rinsed in distilled water, ultrasonically cleaned in trichloroethane and rinsed with a succession of toluene, acetone and ethanol; however, conventional high vacuum compatible cleaning methods can be employed.

After cleaning, the implant was placed on the electrode holder inside the chamber. The chamber was closed and pumped down to show a vacuum of about $5 \times 10^{-5}$ torr. The chamber was then cleaned with an oxygen plasma ($O_2$ pressure, 200 millitorr; RF power, 150 W) for 5 minutes to remove any traces of residue or contamination.

The process of reactive ion etch was carried out in two stages, (a) an oxide "breakthrough" step and a (b) reactive ion etching step. A reactive mixture of $Cl_2$ and $BCl_3$ was used along with the noble gas He as the reaction gases.

(a) Oxide breakthrough—A mixture of $BCl_3$ (20 sccm), $Cl_2$ (10 sccm) and He (30 sccm) was introduced in the chamber and the pressure inside the chamber is maintained at 50 millitorr (sccm=standard centimeter cube per minute). The RF power source was operated in the voltage mode. The power is turned on and the sheath voltage across the plasma and the implant work piece is maintained at 300 V. The power reads 200 Watts. The process time is only 30 seconds.

(b) Reactive Etch—The reactive mixture ratio then was altered to $BCl_3$ (15 sccm) and $Cl_2$ (20 sccm) and He remained same at 30 sccm. The pressure was reduced to 40 millitorr. The RF power source is now operated in the power mode. The power is turned on and maintained at 100 W. The sheath voltage reads 250 V. The process time is 1 hr.

After etching was completed, the power was turned off and the chamber was evacuated of its reactive gases to a pressure of $5\times10^{-5}$ torr. $O_2$ was then introduced inside the chamber (30 sccm) the pressure inside the chamber is set at 200 millitorr. The RF power is turned on to 150 W and the cleaning process time is 15 minutes. This removes any residual hydrocarbon contamination on the surface of the implant work piece. The titanium work piece was then taken out and ultrasonically cleaned.

FIG. 2 is a photomicrograph of the titanium surface after the foregoing treatment. The surface is porous and uneven after surface treatment and spongelike or coral-like in appearance. The micropores are about 1.0 to 2 microns in diameter and about 2 to 3 micron deep. Such a rough and microporous surface can then be coated with extremely thin or thick HA coating to enhance bioactivity at the surface.

Example 2. This is an example to demonstrate modifying a Ti alloy surface. The work piece is made of A work piece made of titanium alloyed with vanadium and aluminum (Ti-6Al-4V) is thoroughly cleaned before it is loaded in the vacuum chamber. The implant is rinsed in distilled water, ultrasonically cleaned in trichloroethane and rinsed with a succession of toluene, acetone and ethanol.

After cleaning, the implant is placed on the electrode holder inside the chamber. The chamber is cleaned with an oxygen plasma ($O_2$ pressure, 200 millitorr; RF power, 150 W) to remove any traces of residue or contamination. The process of reactive ion etch may be carried out in two stages, (a) an oxide "breakthrough" step and a (b) reactive ion etching step, as described in Example 1. A reactive mixture of $Cl_2$ and $BCl_3$ may be used along with the noble gas He as the reaction gases. The alloyed aluminum and vanadium in the titanium work piece promote the non-uniform etch rate of the surface to obtain a microporous surface with interconnection porosity.

Example 3. This example illustrates the preparation of an hydroxyapatite coated work piece.

A work piece is surface treated as described in either Example 1 or 2. The microporous surface is then coated with a thin hydroxyapatite coating as described in U.S. Pat. No. 5,543,019 to Lee et al. The resultant article has a thin hydroxyapatite coating which is sufficiently thin so as not to diminish the porosity of the titanium surface.

Example 4. This example illustrates the osseal in-growth into the surface of the invention.

The purpose of this study was to determine the rate at which the test surfaces of a medical implant is fully integrated into living bone tissue in canines, which were chosen because historically they have historically been used for dental and orthopedic research. Twenty-four animals were used—four groups of three male dogs and four groups of three female dogs at one year old.

Phase I. Bilateral extractions of the mandibular premolars (PM1–PM4) and the first molar (M1) were performed. The procedure was performed under full anesthesia and aseptic surgical conditions. Prior to extractions, maxillary and mandibular impressions were made with the aid of custom trays and polyvinylsiloxane heavy bodied and light bodied material (Express, #M,Minneapolis-St. Paul).

The animals were anesthetized with Acepromazine (1.0 mg/kg i.m.) and sodium penabarbital (25 mg/kg i.m.). The animal's vital signs were taken before and throughout the procedure. The animal was then tested for proper anesthetic depth by applying pressure to the pad of the foot and observing for a response. After obtaining adequate anesthesia, a full thickness mucoperiosteal flap is raised adjacent to the mandibular premolars with the use of a #15 scapula blade and a periosteal elevator. The teeth were then hemisected through their furcation using a small fissure burr in a high speed hand piece with irrigation. Extractions of the separated PM1–PM4 and M1 teeth were performed using elevators and forceps. Guided Tissue Augmentation Membranes (GTAM) were subsequently placed over the extraction sites followed by flap closure with single interrupted 4-0 Gortex® sutures (W. L. Gore, Flagstaff, Ariz.). Bicilline (600,000 u, i.m.) was administered every 48 hours up to six days and Ibuprofen (400 mg/day) up to four days post surgery to each dog for infection and pain control. During recovery, each dog was monitored in a recovery cage until awakening. In order to achieve maximum alveolar bone healing, a three month post extraction healing period was necessary. The animals were kept on a soft diet due to teeth loss resulting from this procedure.

Phase II. In each of the study groups of three dogs, one dog was given a comparison rough surface titanium screw implant, one dog was given a titanium screw implant having the porous surface of the invention and one dog was given a titanium screw implant having a thin HA coating over the porous surface of the invention. The surface of 8 mm long, 3.3 mm diameter Hollow Screw Implants (Institute Straumann, AG, Waldenburg Switzerland) were subjected to the titanium plasma surface treatment of the invention. Calcium phosphate coatings were subsequently applied to half of these implants.

After three months post extraction, surgical implantation was performed. Preparation of the implant bed involved a traumatic surgical techniques under sterile conditions. The anesthesia protocol is that described in Phase I. After obtaining adequate anesthesia l thickness mucoperiosteal flaps we aised bilaterally over the healed mandibular extraction sites, followed by removal of the GTAM. During implant bed preparation, drilling procedures were carried out at rotations of 400 to 600 rpm and under continuous cooling using an $H_2O$. Five implant sites were prepared 8 mm apart in the mandible bilaterally. Penetration of the cortical bone surface of the healed alveolar ridge was accomplished with round burs of diameter 1.4 a nd 2.3 mm. The implant beds were prepared to a depth of 8 mm by means of 2.2 and 2.8 mm drills. Eight mm implants were chosen in order to achieve primary stability without encroaching upon the inferior alveolar nerve and vessels. Twist drills with a diameter of 3.3 were subsequently used to obtain the final bed dimensions.

Figure 18:
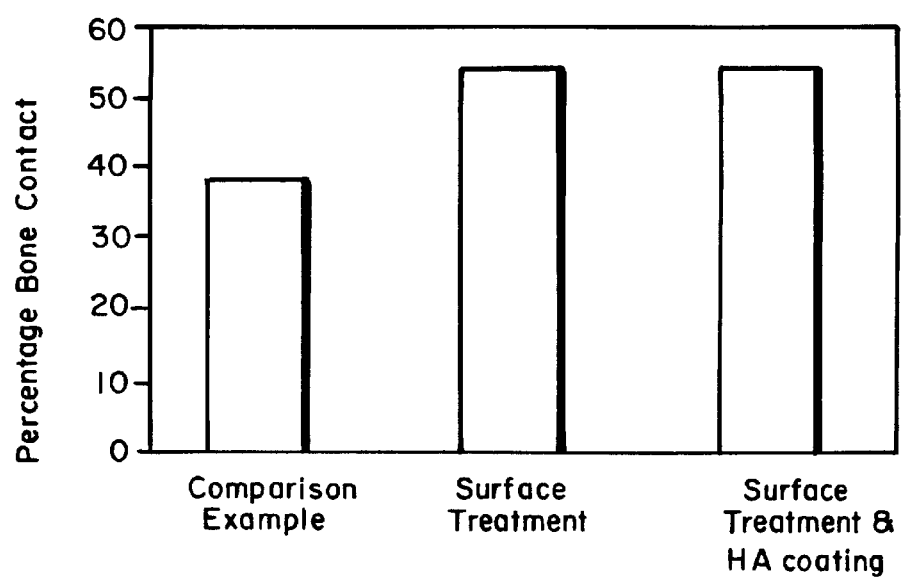
FIG. 18 is a graph of illustrating bone contact (%) for various implants after six months in vivo implantation in dogs.

Phase III. X-rays were taken monthly throughout the study. At the end of six months, the animals were sacrificed and the tests sites were removed and examined by histology. FIG. 18 is a graph illustrating the extent of bone contact with the implant after six months. The screws having the interconnecting porosity of the present invention demonstrated significantly greater bone in-growth than the comparison roughened surface. There was little or no difference in screws with or without the hydroxyapatite coating.

Example 5. This example illustrates use of a medical implant device treated as described in Example 1. A bone filler paste is prepared according to copending application Ser. No. 08/729,344. Bilateral tooth extractions and rough surface titanium screw implants are prepared according to Example 4. Following extraction the tooth socket is filled with the paste and the implant is inserted into the paste prior to paste hardening. The subject is allowed to heal for three months at which time prosthetic teeth are attached to the embedded screw.

Examples 6–12. A series of titanium implant devices were subjected to a plasma etch according to the procedure set forth in Example 1 and process using the conditions described in Table 1, below. Screws were mounted either head down, with the tail extending upward-into the plasma cloud or were mounted horizontally within the plasma cloud. The surface morphology of the result and devices are show in FIGS. 3–12. These experiments demonstrate that a wide variety of surface features may be obtained using the method of the invention to provide articles with novel and desirable surface features.

TABLE 1

Surface treatment parameters for Examples 6–12.

Figure 7:
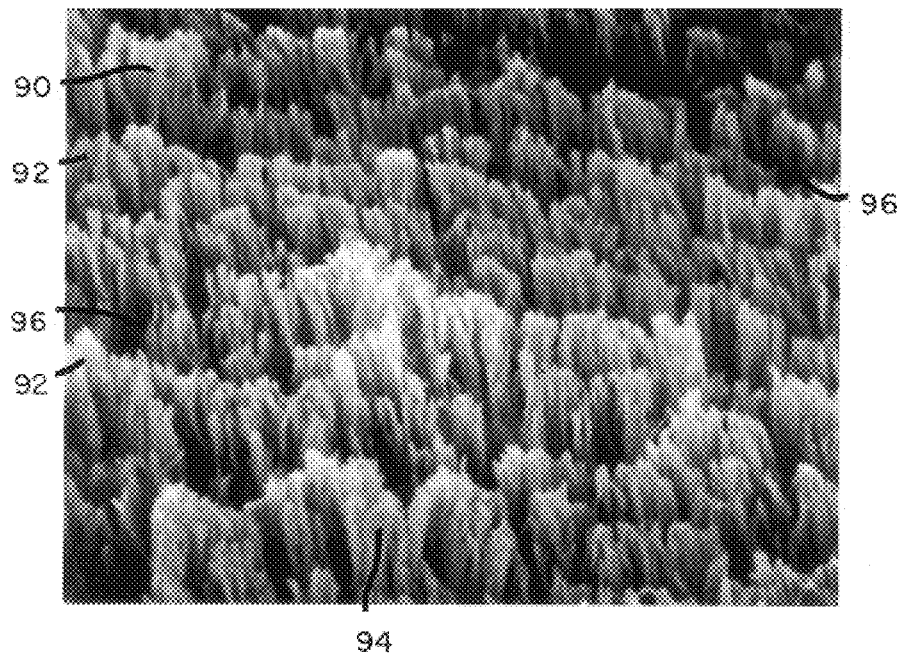
FIG. 7 is a scanning electron photomicrograph (SEM) of a titanium surface after treatment according to the invention at 10,000× magnification.
Figure 8:
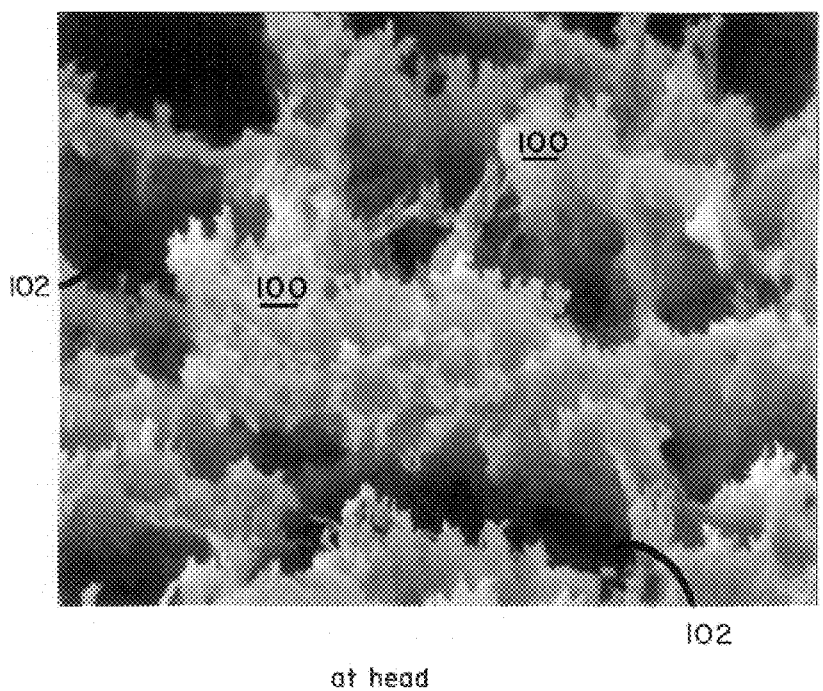
FIG. 8 is a scanning electron photomicrograph (SEM) of a titanium surface after treatment according to the invention at 10,000× magnification.
Figure 9:
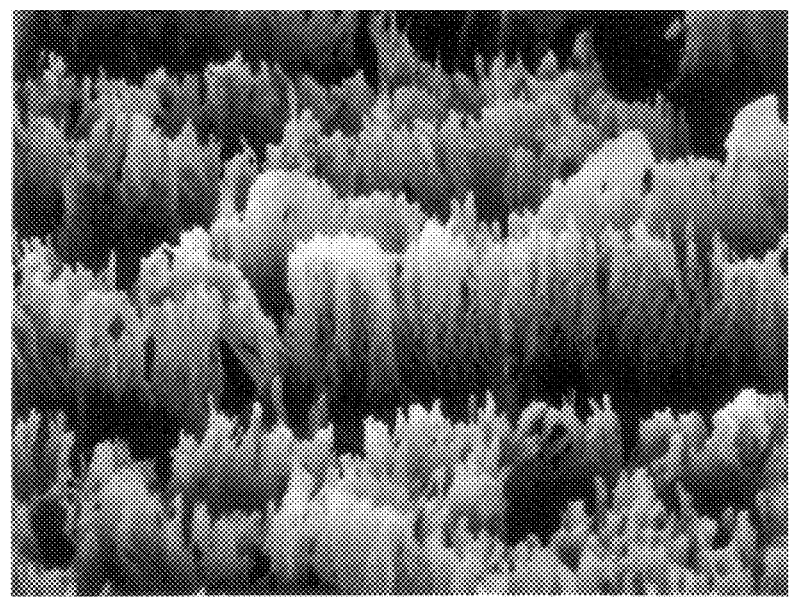
FIG. 9 is a scanning electron photomicrograph (SEM) of a titanium surface after treatment according to the invention at 10,000× magnification.
Figure 10:
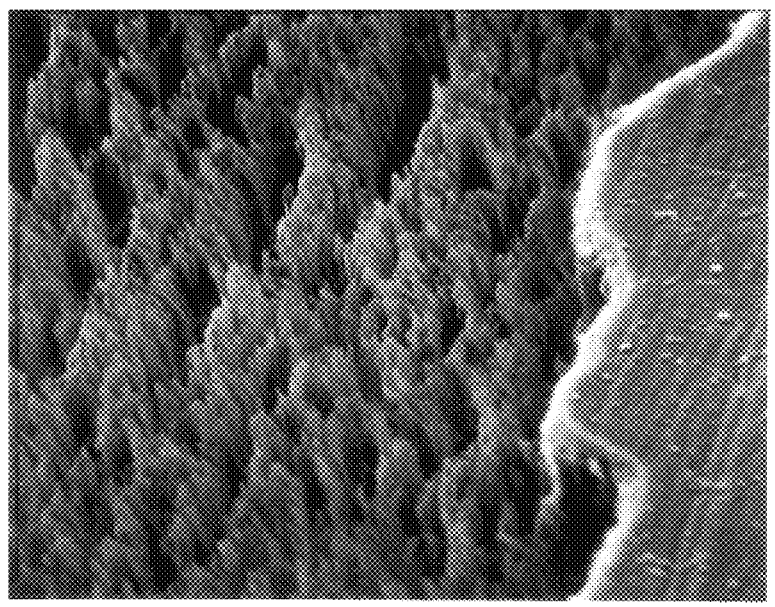
FIG. 10 is a scanning electron photomicrograph (SEM) of a titanium surface after treatment according to the invention at 5,000× magnification showing a masked untreated portion of the surface.
Figure 11:
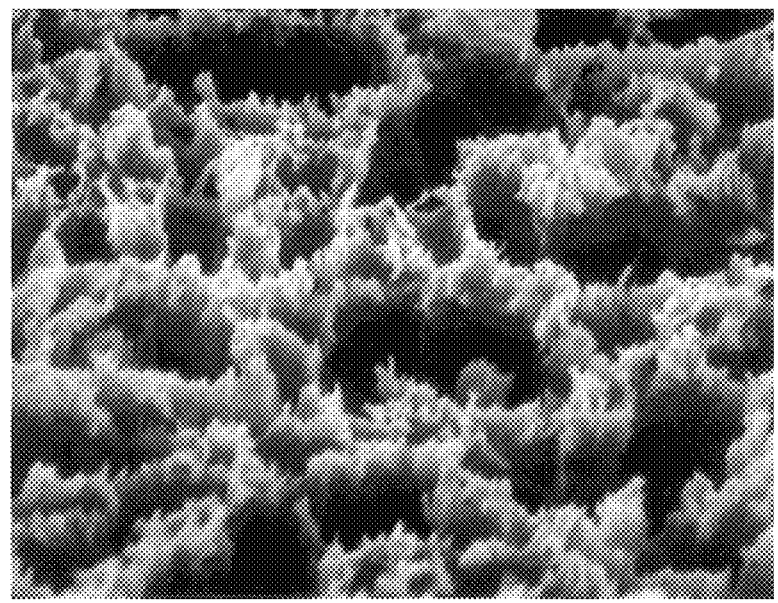
FIG. 11 is a scanning electron photomicrograph (SIM) of a titanium surface after treatment according to the invention at 10,000× magnification.
Figure 12:
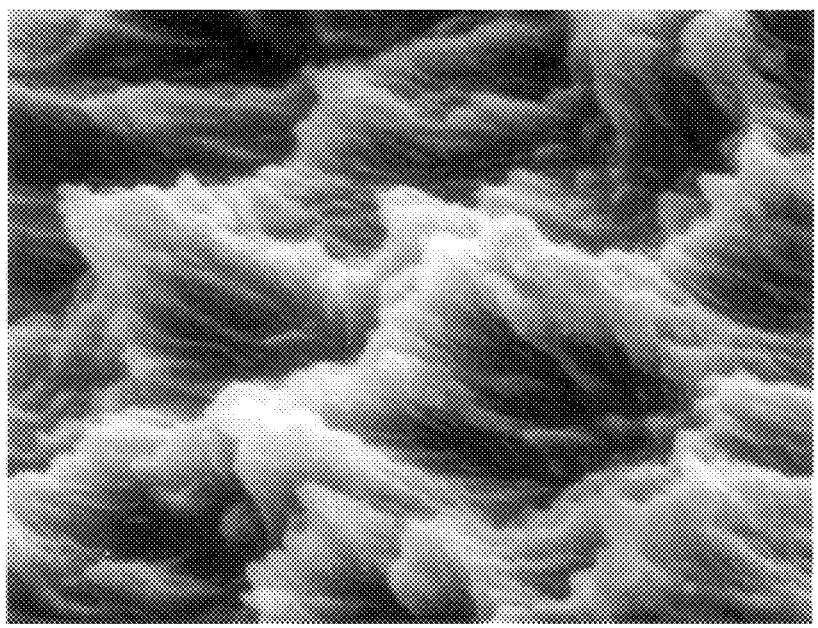
FIG. 12 is a scanning electron photomicrograph (SEM) of a titanium surface after treatment according to the invention at 25,000× magnification.
Figure 13:
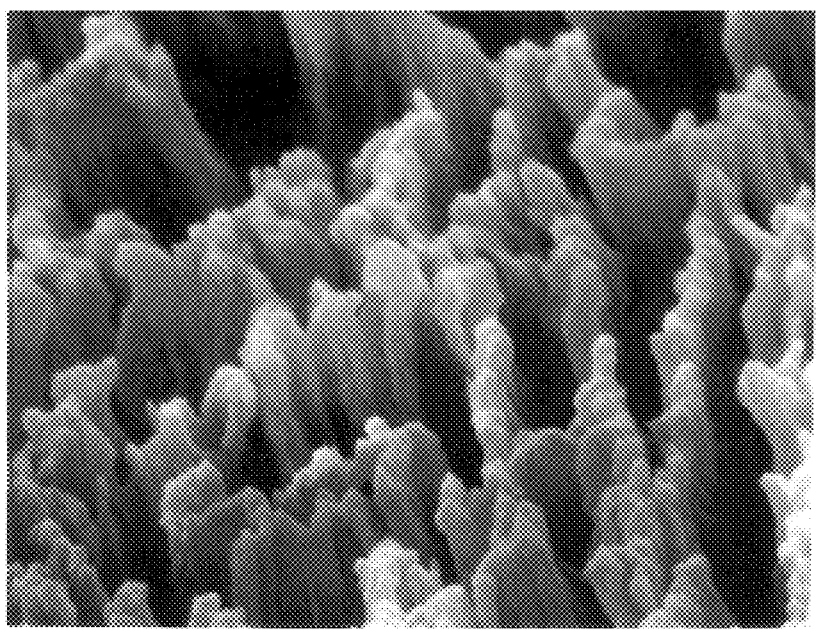
FIG. 13 is a scanning electron photomicrograph (SEM) of a titanium surface after treatment according to the invention at 25,000× magnification.
Figure 14:
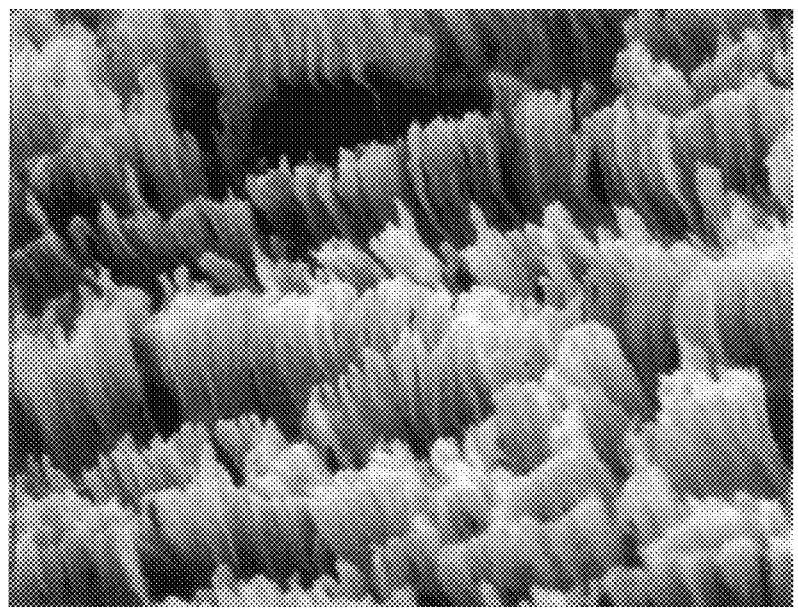
FIG. 14 is a scanning electron photomicrograph (SEM) of a titanium surface after treatment according to the invention at 10,000× magnification.
Figure 15:
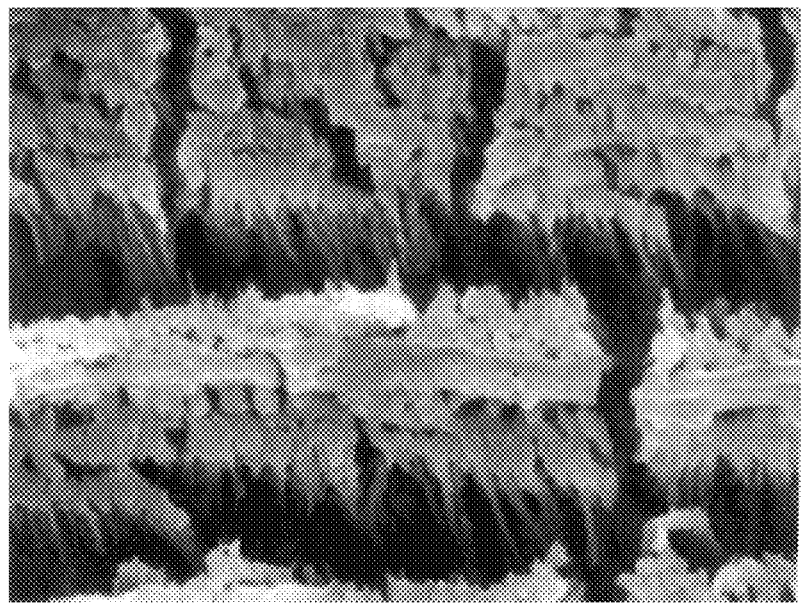
FIG. 15 is a scanning electron photomicrograph (SEM) of a titanium surface after treatment according to the invention at 10,000× magnification.
Figure 16:
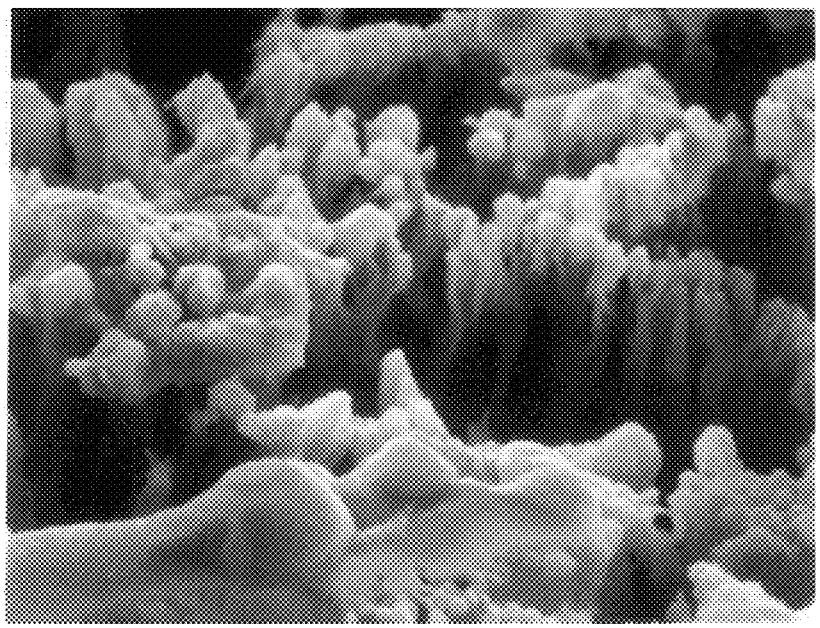
FIG. 16 is a scanning electron photomicrograph (SEM) of a titanium surface after treatment according to the invention at 10,000× magnification.

| Example No. | Process step | Duration (min) | BCl$_3$ (sccm) | Cl$_2$ (sccm) | He/O$_2$ (sccm) | R.F. power (W) | Voltage (V) | pressure (mTorr) | sample location | Surface features shown in: |
|---|---|---|---|---|---|---|---|---|---|---|
| 6  | breakthrough | 0:30  | 20 | 15 | 30 |     | 300 | 50  | vertical | FIG. 9; |
|    | etch         | 75:00 | 15 | 20 | 30 | 100 | 300 | 40  |          | FIG. 11 |
|    | clean        | 15:00 | 0  | 0  | 30 | 150 | 300 | 200 |          |         |
| 7  | breakthrough | 0:45  | 20 | 15 | 30 |     | 300 | 60  | vertical | FIG. 8  |
|    | etch         | 60:00 | 15 | 25 | 30 | 100 | 300 | 80  |          |         |
|    | clean        | 15:00 | 0  | 0  | 30 | 150 | 300 | 200 |          |         |
| 8  | breakthrough | 0:30  | 20 | 15 | 30 |     | 300 | 50  | vertical | FIG. 16 |
|    | etch         | 60:00 | 10 | 25 | 30 | 100 | 300 | 50  |          |         |
|    | clean        | 15:00 | 0  | 0  | 30 | 150 | 300 | 200 |          |         |
| 9  | breakthrough | 0:30  | 20 | 15 | 30 | 225 | 300 | 50  | vertical | FIG. 13 |
|    | etch         | 75:00 | 15 | 25 | 30 | 100 | 175 | 40  |          | FIG. 15 |
|    | clean        | 15:00 | 0  | 0  | 30 | 150 | 75  | 200 |          |         |
| 10 | breakthrough | 0:30  | 20 | 15 | 30 | 250 | 300 | 50  | vertical | FIG. 5; |
|    | etch         | 75:00 | 10 | 25 | 30 |     | 300 | 40  |          | FIG. 10 |
|    | clean        | 15:00 | 0  | 0  | 30 | 150 | 300 | 200 |          | FIG. 14 |
| 11 | breakthrough | 0:30  | 20 | 15 | 30 | 200 | 300 | 50  | vertical | FIG. 4  |
|    | etch         | 60:00 | 10 | 25 | 30 | 125 | 275 | 40  |          |         |
|    | clean        | 15:00 | 0  | 0  | 30 | 150 | 150 | 200 |          |         |
| 12 | breakthrough | 0:30  | 20 | 15 | 30 | 180 | 300 | 50  | horizontal | FIG. 7 |
|    | etch         | 75:00 | 15 | 25 | 30 | 75  | 170 | 40  | in the   |         |
|    | clean        | 15:00 | 0  | 0  | 30 | 150 | 175 | 200 | cloud    |         |

Other embodiments of the invention will be apparent to those skilled in the art from a consideration of this specification or practice of the invention disclosed herein. It is intended that the specification and example be considered as exemplary only, with the true scope and spirit of the invention being indicated by the following claims.

What is claimed is:

1. An article, comprising:
a metallic substrate having a surface comprising metallic filamentous elements having a length of about one to fifteen micrometers, each filamentous element having a first end integral with the substrate and extending in a substantially outward direction from the substrate, wherein at least two filamentous elements have spaced apart first ends and merge at a location a distance from the substrate.

2. The article of claim 1, wherein the merged filamentous elements form arches on the surface of the substrate.

3. The article of claim 1, , or , wherein the metallic surface comprises titanium.

4. The article of claim 1, , or , wherein the article is a medical implant.

5. The article of claim 1, , or , wherein the filamentous elements on the substrate have a density of about 1–40 filamentous elements/$\mu$m$^2$.

6. The article of claim 2, wherein the arched filamentous elements on the substrate have an arch density of about 0.01–10 arches/$\mu$m$^2$.

7. An article, comprising:
a metallic substrate having a surface comprising metallic filamentous elements, each filamentous element having a first end integral with the substrate and extending in a substantially outward direction from the substrate, wherein at least one plurality of filamentous elements collectively form a pattern, each plurality of filamentous elements collectively defining a wall or a ridge on the surface of the substrate.

8. The article of claim 7, wherein at least one wall or ridge is separated from an adjacent wall or ridge by a distance of about 0.5 $\mu$m to about 2 $\mu$m.

9. The article of claim 3, wherein the metallic substrate comprises a titanium alloy.

10. The article of claim 9, wherein the titanium alloy comprises an element selected from the group consisting of aluminum and vanadium.

11. The article of claim , wherein the irregular morphology forms a pattern defining tufts of filamentous elements on the surface of the substrate.

12. An article, comprising:
a metallic substrate having a surface comprising metallic filamentous elements having a length of about one to fifteen micrometers, each filamentous element having a first end integral with the substrate and extending in a substantially outward direction from the substrate, wherein at least one plurality of filamentous elements are joined at first ends and expand outwardly from the joined ends.

13. The article of claim , wherein a plurality of the outwardly extending filamentous elements collectively provides a morphology resembling a member of the group consisting of fingers, tufts, sponges and fans.

14. The article of claim 1, 12, or , wherein the filamentous element length is in the range of about 2 to 3 microns.

15. The article of claim 7 or , wherein adjacent filamentous elements are fused along the entire length thereof.

16. The article of claim 1, 7, 12 or , wherein adjacent filamentous elements are fused over a portion of the length thereof.

17. The article of claim 1, wherein the merged filamentous elements form pores with the substrate, the pores having a pore size of up to about 1 micron.

18. The article of claim 1, wherein the merged filamentous elements form pores with the substrate, the pores having a pore size in the range of about 0.05–0.5 microns.

19. The article of claim 1, wherein the merged filamentous elements form an alcove with the surface of the substrate.

20. The article of claim 7, wherein the wall or ridge further includes free ends of the filamentous elements projecting above the top of the wall or ridge.

21. An article, comprising:
a metallic substrate having a surface comprising metallic filamentous elements, each filamentous element having a first end integral with the substrate and extending in a substantially outward direction from the substrate, wherein a plurality of filamentous elements are positioned and arranged to collectively define undercuts with respect to the surface of the substrate.

22. The article of claim 1, wherein the merged filamentous elements are arranged to collectively define undercuts with respect to the surface of the substrate.

23. The article of claim 1, wherein the merged filamentous elements are arranged to form undercuts on the surface of the substrate.

24. The article of claim 1, wherein pores are formed between the merged filamentous elements, the pores having a pore size of up to about 1 micron.

25. The article of claim 1, wherein pores are formed between the merged filamentous elements, the pores having a pore size in the range of about 0.05–0.5 microns.

* * * * *

UNITED STATES PATENT AND TRADEMARK OFFICE
CERTIFICATE OF CORRECTION

PATENT NO.   : 6,582,470 B1
DATED        : June 24, 2003
INVENTOR(S)  : Dosuk D. Lee and Atul Nagras It is certified that error appears in the above-identified patent and that said Letters Patent is hereby corrected as shown below:

Column 15,
Line 55, delete claim 3 in its entirety and replace it with the following claim 3:
-- The article of claim 1, 12, or 21, wherein the metallic surface comprises titanium. --.
Line 57, delete claim 4 in its entirety and replace it with the following claim 4:
-- The article of claim 1, 12, or 21, wherein the article is a medical implant. --.
Line 59, delete claim 5 in its entirety and replace it with the following claim 5:
-- The article of claim 1, 12, or 21, wherein the filamentous elements on the substrate have a density of about 1-40 filamentous elements/μm2. --.

Column 16,
Line 42, delete claim 11 in its entirety and replace it with the following claim 11:
-- The article of claim 21, wherein the irregular morphology forms a pattern defining tufts of filamentous elements on the surface of the substrate. --.
Line 54, delete claim 13 in its entirety and replace it with the following claim 13:
-- The article of claim 12, wherein a plurality of the outwardly extending filamentous elements collectively provides a morphology resembling a member of the group consisting of fingers, tufts, sponges and fans. --.
Line 58, delete claim 14, in its entirety and replace it with the following claim 14:
-- The article of claim 1, 12 or 21, wherein the filamentous elements length is in the range of about 2 to 3 microns. --.
Line 60, delete claim 15 in its entirety and replace it with the following claim 15:
-- The article of claim 7 or 21, wherein adjacent filamentous elements are fused along the entire length thereof. --.
Line 62, delete claim 16 in its entirety and replace it with the following claim 16:
-- The article of claim 1, 7, 12 or 21, wherein adjacent filamentous elements are fused over a portion of the length thereof. --.

Signed and Sealed this

Seventh Day of October, 2003

JAMES E. ROGAN
*Director of the United States Patent and Trademark Office*